United States Patent
Matsumoto et al.

(10) Patent No.: US 10,960,380 B2
(45) Date of Patent: Mar. 30, 2021

(54) ADSORBENT AND METHOD FOR PRODUCING THE SAME

(71) Applicants: JNC CORPORATION, Tokyo (JP); SofSera Corporation, Tokyo (JP)

(72) Inventors: Yoshihiro Matsumoto, Kumamoto (JP); Akihiro Uchida, Kumamoto (JP); Yasuto Umeda, Kumamoto (JP)

(73) Assignees: JNC CORPORATION, Tokyo (JP); SofSera Corporation, Tokyo (JP)

( * ) Notice: Subject to any disclaimer, the term of this patent is extended or adjusted under 35 U.S.C. 154(b) by 192 days.

(21) Appl. No.: 15/384,326

(22) Filed: Dec. 20, 2016

(65) Prior Publication Data

US 2017/0182478 A1 Jun. 29, 2017

(30) Foreign Application Priority Data

Dec. 28, 2015 (JP) ............... JP2015-256003

(51) Int. Cl.
| | |
|---|---|
| *B01J 20/282* | (2006.01) |
| *B01D 15/38* | (2006.01) |
| *B01J 20/30* | (2006.01) |
| *C01B 25/32* | (2006.01) |
| *C07K 1/16* | (2006.01) |
| *C07K 16/06* | (2006.01) |
| *C12N 9/36* | (2006.01) |

(52) U.S. Cl.
CPC ........ *B01J 20/282* (2013.01); *B01D 15/3809* (2013.01); *B01J 20/3028* (2013.01); *B01J 20/3078* (2013.01); *C01B 25/32* (2013.01); *C07K 1/16* (2013.01); *C07K 16/065* (2013.01); *C12N 9/2462* (2013.01); *C12Y 302/01017* (2013.01); *C12Y 304/21001* (2013.01); *C07K 2317/21* (2013.01); *C07K 2317/55* (2013.01)

(58) Field of Classification Search
CPC .. B01J 20/282; B01J 20/3028; B01J 20/3078; B01D 15/3809; C01B 25/32; C07K 1/16; C07K 16/065
See application file for complete search history.

(56) References Cited

U.S. PATENT DOCUMENTS

| | | | |
|---|---|---|---|
| 4,781,904 A | 11/1988 | Tagaya et al. | |
| 4,794,171 A | 12/1988 | Tagaya et al. | |
| 2006/0257306 A1 | 11/2006 | Yamamoto et al. | |
| 2012/0252098 A1 | 10/2012 | Gagnon | |
| 2012/0285880 A1 | 11/2012 | Kobayashi | |
| 2015/0024023 A1* | 1/2015 | Gibson | ........... C01B 25/32 424/423 |
| 2017/0014798 A1 | 1/2017 | Kobayashi | |

FOREIGN PATENT DOCUMENTS

| | | |
|---|---|---|
| EP | 0252472 | 1/1988 |
| JP | S62070212 | 3/1987 |
| JP | S62091410 | 4/1987 |
| JP | S63016044 | 1/1988 |
| JP | S63016045 | 1/1988 |
| JP | H03021342 | 1/1991 |
| JP | H04118047 | 4/1992 |
| JP | H0517111 | 1/1993 |
| JP | 2005082465 | 3/2005 |
| JP | 2005313150 | 11/2005 |
| JP | 2006315871 | 11/2006 |
| JP | 2011068539 | 4/2011 |
| JP | 2013538357 | 10/2013 |

OTHER PUBLICATIONS

Freitag, R., and Hilbrig, F., 2012, Isolation and purification of recombinant proteins, antibodies, and plasmid DNA with hydroxyapatite chromatography, Biotech. J. 7:90-102.*

Ruth Freitag, et al., "Isolation and purification of recombinant proteins, antibodies and plasmid DNA with hydroxyapatite chromatography," Biotechnology Journal, vol. 7, No. 1, Jan. 2012, pp. 90-102.

"Office Action of Japan Counterpart Application," with English translation thereof, dated May 14, 2019, pp. 1-8.

"Office Action of Japan Counterpart Application," with English translation thereof, dated Oct. 8, 2019, pp. 1-6.

* cited by examiner

*Primary Examiner* — Jeffrey S Parkin
(74) *Attorney, Agent, or Firm* — JCIPRNET

(57) ABSTRACT

An adsorbent, which can be produced by a method in which a particle size, a pore size, a specific surface area or the like can be easily controlled, and is suitable for isolation of biomolecules. The adsorbent contains aggregates of calcium phosphate-based particles, and has an average pore size of 15 to 36 nanometers and a specific surface area of 40 to 90 $m^2/mL$ when measurement is carried out by mercury porosimetry.

16 Claims, No Drawings

ADSORBENT AND METHOD FOR PRODUCING THE SAME

CROSS-REFERENCE TO RELATED APPLICATIONS

This application claims the priority benefit of Japan application serial no. 2015-256003, filed on Dec. 28, 2015. The entirety of the above-mentioned patent application is hereby incorporated by reference herein and made a part of this specification.

TECHNICAL FIELD

The invention relates to an adsorbent containing calcium phosphate-based particles and a method for producing the same.

BACKGROUND ART

Operation of purifying various substances by utilizing a substance having adsorption action as a media for chromatography is widely known, and an object and impurities are separated by utilizing various molecular interactions between the media and a substance to be isolated. For example, as such materials of the media for liquid chromatography, inorganic materials such as silica, alumina, zirconia and titania, natural polymers such as cellulose, synthetic polymers such as a styrene-divinylbenzene copolymer and polymethacrylate, and carbon are used.

In addition thereto, an attempt has also been made on utilizing a calcium phosphate-based compound, in particular hydroxyapatite $(Ca_{10}(PO_4)_6(OH)_2)$ as an adsorbent. Hydroxyapatite is known to exhibit high adsorptivity on biomolecules such as amino acid, protein, lipid and sugar. Hydroxyapatite has been utilized by taking advantage of such characteristics as the media for column chromatography, the media being used for isolating the biomolecules or the like, and as cosmetics for the purpose of adsorbing and removing superfluous lipid and waste, or the like.

Patent literature Nos. 1 to 7 and Non-Patent literature No. 1 disclose use of calcium phosphate-based compound as a media for chromatography. In order to obtain a media having desired isolation characteristics, development has been made on hydroxyapatite having specific crystal structure (Patent literature Nos. 1 and 2), a media prepared by coating a calcium phosphate-based compound on a surface of substrate (Patent literature Nos. 4 and 6), an adsorption-isolating agent using calcium phosphate-based porous granules having continuous pore structure of two kinds of sizes (Patent literature No. 5), a media for chromatography being formed of aggregates of hydroxyapatite particles (Patent literature No. 7), and so forth. Moreover, various attempts have been made also on a method for producing the media. For example, Patent literature No. 3 discloses a method for obtaining a media for liquid chromatography by mixing thermally decomposable particles in calcium phosphate-based particles and granulating the resulting mixture, and then calcining the granulates at a high temperature. Moreover, Patent literature No. 7 discloses a method for obtaining calcium phosphate aggregates that can be used as a media for chromatography by charging primary particles of calcium phosphate into a solvent to cause aggregation of the particles.

A number of media have been thus developed. However, a never-ending challenge in the field of the media for chromatography is to develop an adsorbent having adsorption characteristics with regard to adsorption force, a pore size, a specific surface area or the like suitable for a substance according to various object substances and/or having isolation characteristics.

CITATION LIST

Patent Literature

Patent literature No. 1: JP S62-70212 A
Patent literature No. 2: JP S62-91410 A
Patent literature No. 3: JP S63-16045 A
Patent literature No. 4: JP S63-16044 A
Patent literature No. 5: JP H3-21342 A
Patent literature No. 6: JP 2005-313150 A
Patent literature No. 7: JP 2005-82465 A

Non-Patent Literature

Non-patent literature No. 1: Ruth, Freitag, "Isolation and purification of recombinant proteins, antibodies and plasmid DNA with hydroxyapatite chromatography", Biotechnology Journal, 2012, vol. 7, pp. 90-102.

SUMMARY OF INVENTION

Under the background described above, an adsorbent having adsorption and/or isolation characteristics suitable for an object substance has been required. Moreover, in order to easily obtain a plurality of kinds of adsorbents that can be applied to various substances, the adsorbents are desired to be produced by a method according to which a particle size, a pore size, a specific surface area or the like can be easily controlled.

The present inventors have diligently continued to conduct study in order to solve the problem described above. As a result, the present inventors have found that an adsorbent for biomolecules such as protein and having a desired pore size and specific surface area according to an object substance can be provided by spray-drying slurry containing calcium phosphate-based particles having an average major-axis size of 20 to 250 nanometers, and controlling calcination conditions. The invention is as described below, for example.

Item 1. An adsorbent, containing aggregates of calcium phosphate-based particles, and having an average pore size of 15 to 36 nanometers and a specific surface area of 40 to 90 $m^2/mL$ when measurement is carried out by mercury porosimetry.

Item 2. The adsorbent according to item 1, wherein the calcium phosphate-based particles are hydroxyapatite particles.

Item 3. The adsorbent according to item 1 or 2, wherein the calcium phosphate-based particles (primary particles) have an average major-axis size of 20 to 50 nanometers.

Item (3-1). The adsorbent according to any one of items 1 to 3, wherein the aggregates (secondary particles) of the calcium phosphate-based particles have an average particle size of 10 to 200 micrometers.

Item (3-2). The adsorbent according to any one of items 1 to 3-1, having an average particle size of 10 to 200 micrometers.

Item 4. The adsorbent according to any one of items 1 to 3-2, being used as a media for chromatography for isolation and purification of a biomolecule.

Item 5. The adsorbent according to item 4, wherein the biomolecule is a protein.

Item 6. The adsorbent according to item 5, wherein the protein has a weight average molecular weight less than 60 kDa.

Item 7. The adsorbent according to item 6, wherein the dynamic binding capacity of the protein is 30 mg/mL or more in a retention time of 4 minutes.

Item 8. The adsorbent according to item 7, wherein the protein is a fragmented antibody, and the dynamic binding capacity is 30 mg/mL or more.

Item 9. The adsorbent according to item 7, wherein the protein is lysozyme, and the dynamic binding capacity is 35 mg/mL or more.

Item 10. The adsorbent according to item 7, wherein the protein is α-chymotrypsinogen A, and the dynamic binding capacity is 70 mg/mL or more.

Item 11. A media for chromatography, containing the adsorbent according to any one of items 1 to 10.

Item 12. A method for purifying a biomolecule, including isolation and purification of the biomolecule by using the adsorbent according to any one of items 1 to 10.

Item 13. The method according to item 12, wherein the biomolecule is a protein.

Item 14. The purification method according to item 13, wherein the protein is a fragmented antibody.

Item 15. The purification method according to item 14, wherein the fragmented antibody is a Fab fragment.

Item 16. A method for producing an adsorbent, including:

(a) spray-drying slurry containing calcium phosphate-based particles (primary particles) having an average major-axis size of 20 to 50 nanometers to obtain aggregates (secondary particles) of calcium phosphate-based particles; and (b) calcining the aggregates (secondary particles) of calcium phosphate-based particles at a temperature of 100 to 700° C.

Item 16-1. The method according to item 16, wherein the adsorbent is the adsorbent according to any one of items 1 to 10.

Item 16-2. The method according to item 16 or 16-1, wherein the slurry contains the calcium phosphate-based particles in an amount of 10% to 50% by weight based on the solvent.

According to the invention, an adsorbent particularly suitable for isolation of biomolecules can be provided. Moreover, the adsorbent of the invention can be produced by a method according to which a particle size, a pore size, a specific surface area or the like can be easily controlled.

DESCRIPTION OF EMBODIMENTS

Hereinafter, embodiments of the invention will be described in detail.

1. Method for Producing an Adsorbent

First, a method for producing an adsorbent will be described. The method for producing the adsorbent according to embodiments of the invention includes the following steps (a) and (b) in sequence:

(a) spray-drying slurry containing calcium phosphate-based particles having an average major-axis size of about 20 to about 50 nanometer to obtain aggregates of calcium phosphate-based particles, and (b) calcining the aggregates of calcium phosphate-based particles at a temperature of about 100 to about 700° C.

The adsorbent produced by the method has an average pore size of about 15 to about 36 nanometers and a specific surface area of about 40 to about 90 m$^2$/mL when measurement is carried out by mercury porosimetry, and can be used as a media for chromatography, for example. The adsorbent to be obtained is reasonably described to develop excellent performance particularly in isolation of biomolecules due to characteristics such as a particle size, a pore size and a specific surface area. Moreover, the particle size of the aggregates to be obtained can be controlled by adjusting the concentration and spray-drying conditions of the calcium phosphate-based compound in the slurry to be spray-dried. Further, the pore size, the specific surface area or the like of the adsorbent to be obtained can be controlled by changing the calcination temperature. Therefore, a plurality of kinds of adsorbents that can be applied to various substances can be easily obtained.

Hereinafter, each step described above will be described in the order.

Step A

In step (a), nanoparticles (hereinafter, also referred to as "primary particles" or "calcium phosphate-based particles") containing the calcium phosphate-based compound are dispersed into a solvent to prepare slurry, and then the resulting slurry is spray-dried to obtain the aggregates (hereinafter, also referred to as "secondary particles") of the calcium phosphate-based particles in which the aggregates are formed by aggregating a plurality of the calcium phosphate particles.

Primary Particles and a Method for Producing the Same

The primary particles preferably have an average major-axis size of about 20 to about 50 nanometers, further preferably about 20 to about 40 nanometers, and particularly preferably about 20 to about 30 nanometers. The adsorbent having excellent adsorption ability can be obtained in purification of biomolecules, especially proteins, by using particles having an average major-axis size in the range described above.

Here, the average major-axis size of primary particles means a value measured by the method described below.

Method of Measuring the Average Major Axis of Primary Particles

Particles photographed substantially from just above are selected in the image obtained by photographing the calcium phosphate-based particles at a magnification of 1,000 by using a scanning electron microscope (SEM). Next, two line segments both ends of which are located on an outer periphery of a particle are drawn on the particle. On the above occasion, one line segment is to be a maximum in a length thereof. Moreover, the other line segment is drawn in such a manner that the two line segments are perpendicular to each other at a midpoint each. In the two line segments thus drawn, the length of the shorter line segment is taken as the minor-axis size, and the length of the longer line segment is taken as the major-axis size. Then, 100 particles are taken out sequentially from the particles having a larger major axis, and then an average value (arithmetic average) of the major-axis sizes of the 100 particles is determined, and the obtained value is taken as the average major-axis size of the primary particles. However, particles having blurred contours, particles that excessively come closer to other particles to have blurred boundaries with other particles, particles part of which is hidden in shadows of other particles, and the like are excluded from the measurement objects. In addition, the primary particles herein mean a plurality of hydroxyapatite particles existing in a state of being aggregated. Accordingly, the average major-axis size of the primary particles means an average major-axis size of particles formed by aggregating a plurality of the calcium phosphate particles.

Specific examples of the calcium phosphate-based compound include hydroxyapatite ($Ca_{10}(PO_4)_6(OH)_2$) fluorine apatite ($Ca_{10}(PO_4)_6F_2$), chlorine apatite ($Ca_{10}(PO_4)_6Cl_2$) and tricalcium phosphate ($Ca_3(PO_4)_2$), but are not limited thereto. Above all, hydroxyapatite is preferred in view of high mechanical strength.

The content of the calcium phosphate-based compound in the primary particles is preferably about 50% by weight or more, further preferably about 70% by weight or more, particularly preferably about 90% by weight or more. The primary particles are most preferably monocrystal particles of the calcium phosphate-based compound.

As the primary particles, commercially available particles may be purchased and used, or the particles may be produced and then used. When the calcium phosphate-based compound is hydroxyapatite, specific examples of the primary particles include hydroxyapatite particles (average major-axis size: 24 nanometers) made by Sofsera Corporation, but are not limited thereto. The calcium phosphate-based particles having the average major-axis size described above can also be appropriately used.

When the primary particles are to be produced, the production method is not particularly limited, as long as the nanoparticles containing the calcium phosphate-based compounds can be produced by the method. The method may be appropriately selected according to the kind of calcium phosphate-based compounds, the objective particle size or the like. For example, as described in JP 2002-137910 A, nanoparticles of hydroxyapatite can be produced by solubilizing and mixing a calcium solution and a phosphoric acid solution into a surfactant/water/oil-based emulsion phase, and then allowing the resulting mixture to react at the temperature of the cloudy point of the surfactant or higher. On the above occasion, the size of the hydroxyapatite particles can be controlled by changing a functional group and the hydrophilic/lipophilic ratio of the surfactant. Also when calcium phosphate-based compounds other than the hydroxyapatite are used, the primary particles can also be produced in a manner similar to the method as described above.

When micelles of the surfactant are prepared, the functional group (in particular, a hydrophilic site) of the surfactant and the hydrophilicity/lipophilic ratio are important to cause differences in stability and a cloudy point of the micelles. Moreover, the cloudy point of the surfactant is different also depending on the type of surfactant. Therefore, the stability and the cloudy point of micelles can be changed by appropriately varying the kind of surfactant to be used, and as a result, the size of the calcium phosphate-based particles can be controlled.

In addition, the kind of surfactant to be used is not particularly limited. For example, the surfactant to be used can be appropriately selected from known surfactants such as an anionic surfactant, a cationic surfactant, an amphoteric ionic surfactant, and a nonionic surfactant disclosed in JP 5-17111 A. Above all, from a viewpoint of ease of controlling the shape of crystals, a nonionic surfactant is preferred. Specific examples of the nonionic surfactant include polyoxyethylene alkyl ether, polyoxyethylene allyl ether, polyoxyethylene alkylallyl ether, a polyoxyethylene derivative, an oxyethylene-oxypropylene block copolymer, sorbitan fatty acid ester, polyoxyethylene sorbitan fatty acid ester, polyoxyethylene sorbitol fatty acid ester, glycerol fatty acid ester, polyoxyethylene fatty acid ester and polyoxyethylene alkylamine. Specific examples of the cationic surfactant include quaternary ammonium salt such as stearylamine hydrochloride, lauryl trimethylammonium chloride and alkylbenzenedimethylammonium chloride. Specific examples of the anionic surfactant include higher alcohol sulfates such as sodium lauryl alcohol sulfate and sodium oleyl alcohol sulfate, alkyl sulfates such as sodium lauryl sulfate and ammonium lauryl sulfate, and alkylaryl sulfonates such as sodium dodecylbenzene sulfonate and sodium dodecylnaphthalene sulfonate. Specific examples of the amphoteric surfactant include an alkyl betaine type, an alkylamide betaine type and an amineoxide type. The surfactants can be used alone in one kind or in combination of two or more kinds. In view of the cloudy point and the solubility, pentaethylene glycol dodecyl ether is particularly preferably used.

Specific examples of substances that can be used in the form of an oil phase in the method described above include hydrocarbons such as toluene, xylene, hexane, dodecane and cyclohexane, halogenated hydrocarbons such as chlorobenzene and chloroform, ethers such as diethyl ether, alcohols such as butanol, and ketones such as methyl isobutyl ketone and cyclohexanone. One or more kinds of substances having small solubility in water and having a capability of dissolving the surfactant to be used are selected and used among the substances. From the viewpoint of solubility in water and dissolving the surfactant, dodecane is particularly preferably used.

With regard to the reaction temperature (namely, a temperature equal to or higher than the cloudy point of surfactant), the reaction time, the amount of addition of raw materials or the like, optimum conditions can be appropriately adopted according to the structure of desired primary particles. However, the upper limit of the reaction temperature is preferably a temperature at which the solution does not boil, for example, about 90° C. or lower.

The primary particles obtained as described above can be arbitrarily provided for a washing step with water, a centrifugation step, a filtration step or the like.

Secondary Particles and a Method for Producing the Same

Subsequently, the primary particles obtained as described above are dispersed into a solvent to prepare slurry. A plurality of primary particles are aggregated by spray-drying the slurry, and secondary particles (namely, aggregates of the calcium phosphate-based particles) are formed.

As the solvent for dispersing the primary particles thereinto, water is preferred, but the solvent is not limited thereto. In the solvent, the primary particles are preferably dispersed in an amount of about 10% to about 50% by weight, and further preferably in an amount of about 10% to about 30% by weight. The secondary particles having a suitable particle size can be obtained by dispersing the particles in the solvent in such an amount. More specifically, if the amount of primary particles to be dispersed thereinto is excessively small, the particle size of the secondary particles is liable to become smaller than a desired value. In contrast, if the amount of primary particles is excessively large, the particle size of the secondary particles is liable to become larger than the desired value.

Spray-drying can be performed by means of a known spray-drying apparatus. However, in view of the capability of easily controlling the particle size of the secondary particles, a spray-drying apparatus of a rotary atomizer system is preferably used. The secondary particles having a desired particle size can be obtained by varying a disc shape and rotational speed of the rotary atomizer.

The average particle size of the secondary particles is preferably about 10 to about 200 micrometers, further preferably about 20 to about 100 micrometers, and particularly preferably about to about 80 micrometers. The adsorbent having excellent adsorption and isolation ability can be obtained in purification of biomolecules, particularly proteins by using the secondary particles the average particle size of which is within the range described above. Here, the average particle size of the secondary particles means a volume average size measured by a laser diffraction scattering method.

Spray-drying is preferably performed at about 190 to about 280° C., further preferably at about 190 to about 250° C. The secondary particles can be obtained with a good yield by spray-drying the particles at a temperature within the range described above.

Step (b)

In step (b), the secondary particles are calcined to obtain the adsorbent. The calcination temperature preferably is about 100 to about 700° C., and may be about 100 to about 600° C., about 100 to about 500° C., about 100 to about 400° C., about 100 to about 300° C., about 100 to about 200° C., about 200 to about 700° C., about 200 to about 600° C., about 200 to about 500° C., about 200 to about 400° C., about 200 to about 300° C., about 300 to about 700° C., about 300 to about 600° C., about 300 to about 500° C., about 300 to about 400° C., about 400 to about 700° C., about 400 to about 600° C., about 400 to about 500° C., about 500 to about 700° C., about 500 to about 600° C. or about 600 to about 700° C., for example. Among the above temperature ranges, the particles are calcined preferably at about 200 to about 600° C. or about 300 to about 500° C., for example, in view of satisfying both adsorption and/or isolation characteristics and stability of particles. The heating rate, the maximum temperature, the holding time and the like in the calcination step are important factors to determine characteristics (particularly particle size, porosity, pore size, specific surface area, and so on) of the adsorbent. Therefore, the adsorbent having desired characteristics can be obtained by suitably setting the conditions. The pore size of the adsorbent tends to increase, and on the other hand, the specific surface area tends to decrease by setting the calcination temperature at a high level or increasing a calcination time. Thus, according to the method described above, the adsorbents having various pore sizes and specific surface areas can be produced by adjusting the calcination temperature and the calcination time. Therefore, various adsorbents having adsorption and/or isolation characteristics suitable for the object substances can be obtained by a simple method.

The heating rate during calcination is preferably about 5 to about 20° C. per minute. Moreover, the holding time at the maximum temperature is preferably about 5 to about 240 minutes, and further preferably about 30 to about 120 minutes. The adsorbent having excellent isolation ability can be obtained in purification of biomolecules, particularly protein by calcining the particles under preferred conditions described above.

After the calcination step, operation in the washing step, a drying step and the like may be arbitrarily performed. Moreover, the obtained adsorbent is classified, and only the adsorbent having a desired size can also be sorted out and used.

2. Adsorbent

According to one embodiment of the invention, the adsorbent that can be produced by the method described above is provided. More specifically, the adsorbent containing the aggregates of the calcium phosphate-based particles, and having an average pore size of about 15 to about 36 nanometers and a specific surface area of about 40 to about 90 m$^2$/mL when measurement is carried out by mercury porosimetry are provided. The above adsorbent has excellent adsorption ability and isolation ability in purification of biomolecules, particularly protein, and is preferably used for isolating and purifying the protein. In particular, the adsorbent develops excellent performance as the media for chromatography for isolating and purifying the protein. The protein to be isolated is not particularly limited, but the protein having a relatively low molecular weight is preferred, for example, a protein having a weight average molecular weight less than about 60 kDa is preferred. The weight average molecular weight of the protein is preferably about 10 kDa or more and less than about 60 kDa, further preferably about 20 to about 55 kDa. Specific examples thereof include lysozyme, a fragmented antibody (for example, Fab fragments), scFV, Diabody, erythropoietin, •insulin, interferons, albumin and chymotrypsinogen.

The object substance is not limited thereto, and as mentioned above, the adsorbents having various adsorption and/or isolation characteristics are easily obtained by varying the calcination temperature and/or the calcination time, and therefore a variety of substances can be targeted.

The average particle size of the adsorbent is preferably about 10 to about 200 micrometers, further preferably about 20 to about 100 micrometers, particularly preferably about 30 to about 80 micrometers. The average pore size is preferably about 15 to about 36 nanometers, and further preferably about 16 to about 24 nanometers, when measurement is carried out by mercury porosimetry. The specific surface area is preferably about 40 to about 90 m$^2$/mL, and further preferably about 50 to about 80 m$^2$/mL, particularly preferably about 55 to about 70 m$^2$/mL, when measurement is carried out by mercury porosimetry. Here, the average particle size of the adsorbent means a volume average size measured by a laser diffraction scattering method.

Here, the average pore size is an average value (arithmetic average) of pore diameters as calculated from the following equation (1) (Washburn equation) in the range of about 0.0018 to about 0.95 micrometers during mercury penetration. Moreover, the specific surface area is expressed in terms of a value calculated from the following equation (2).

(pore diameter)=−4×(surface tension of mercury)× cos(contact angle between mercury and sample)/(pressure)   Equation (1)

(specific surface area)=2×(press-in volume of mercury)/(pore radius)/(sample weight)/(degree of swelling)   Equation (2)

According to the invention, the adsorbent having the average particle size, the average pore size and the specific surface area in the ranges described above is obtained, and such values of the average particle size, the average pore size and the specific surface area are preferred in isolation and purification of proteins.

When a protein having a weight average molecular weight less than about 60 kDa is isolated, to take lysozyme, fragmented antibody or α-chymotrypsinogen A as an example, dynamic binding capacity of lysozyme for the adsorbent of the invention is about 35 mg/mL or more (for example, about 35 to about 70 mg/mL or about 35 to about 60 mg/mL), further preferably about 40 mg/mL or more (for example, about 40 to about 70 mg/mL or about 40 to about 60 mg/mL), particularly preferably about 50 mg/mL or more (for example, about 50 to about 70 mg/mL or about 50 to about 65 mg/mL), in terms of the retention time of 4 minutes. Moreover, the dynamic binding capacity of the fragmented antibody is about 30 mg/mL or more (for example, about 30 to about 60 mg/mL or about 30 to about 50 mg/mL), preferably about 35 mg/mL or more (for example, about 35 to about 60 mg/mL or about 35 to about 50 mg/mL), further preferably about 40 mg/mL or more (for example, about 40 to about 60 mg/mL or about 40 to about 50 mg/mL), particularly preferably about 45 mg/mL or more (for example, about 45 to about 60 mg/mL or about 45 to about 50 mg/mL), in terms of the retention time of 4 minutes. Further, the dynamic binding capacity of α-chymotrypsinogen A is about 70 mg/mL or more (for example, about 70 to about 110 mg/mL or about 70 to about 100 mg/mL), preferably about 80 mg/mL or more (for example, about 80 to about 110 mg/mL or about 80 to about 100 mg/mL), further preferably about 90 mg/mL or more (for example, about 90 to about 110 mg/mL or about 90 to about 100 mg/mL), particularly preferably about 95 mg/mL or more (for example, about 95 to about 110 mg/mL or about 95 to about 100 mg/mL), in terms of the retention time of 4 minutes.

In addition, "dynamic binding capacity" herein means 10% dynamic binding capacity as measured in Examples described later.

Thus, the adsorbent of the invention has excellent adsorption and/or isolation properties to a protein having a relatively low molecular weight, in particular a protein having a weight average molecular weight less than about 60 kDa (specifically, lysozyme, fragmented antibody, α-chymotrypsinogen A or the like), and accordingly, the adsorbent is particularly useful for isolation and purification of such protein.

According to one embodiment of the invention, a method of purifying a biomolecule is provided, including isolation and purification of a biomolecule (particularly a protein) by using the adsorbent described above. Moreover, according to another embodiment, a media for chromatography that contains the adsorbent described above is provided.

However, the application of the adsorbent of the invention is not limited to the media for chromatography. The calcium phosphate-based compound, in particular hydroxyapatite has high biocompatibility, and therefore can be widely used in a bone filler, a dental filler, a drug sustained-release agent or the like in the medical field, for example. Moreover, the adsorbent of the invention can also be used as an immobilized carrier for bacteria and yeast, a deodorant, or the like.

EXAMPLES

In the following, the invention will be described in greater detail by way of Examples. However, the invention is not limited by the Examples.

Example 1: Preparation of Aggregates of Hydroxyapatite Particles

Hydroxyapatite spherical particles (primary particles) having an average major-axis size of 24 nm (made by Sofsera Corporation) were dispersed into water to be in a concentration of 20% by weight to prepare slurry. The resulting slurry was spray-dried by SPRAY DRYER LB-8 (made by Ohkawara Kakohki Co., Ltd.) to granulate hydroxyapatite particles into aggregates (secondary particles). Upon granulation, formation of fine particles by spraying was performed by adjusting the rotating speed of the rotary atomizer to 12,800 so as to obtain a desired particle size. Moreover, spray-drying was performed under conditions in which a hot air temperature at a drying chamber inlet was 190° C., the air speed was 6 m$^3$/minute and the amount of slurry supply to SPRAY DRYERLB-8 was 1700 mL/hr.

Calcination Step

Then, 200 g of the hydroxyapatite secondary particles produced as described above was weighed in an alumina crucible, and put in a calcination furnace. The temperature in the furnace was raised to 100° C. at a rate of 10° C. per minute. After the temperature was held at 100° C. for 1 hour, the hydroxyapatite secondary particles were left to cool to about room temperature. Then, a 1% (w/v) aqueous solution of ammonium nitrate in an amount 10 times the amount of the calcined hydroxyapatite particles on weight base was added to the calcined hydroxyapatite particles, and the resulting mixture was subjected to ultrasonic cleaning while the mixture was stirred for 5 minutes. Subsequently, the filtrate was removed by filtration in vacuum, and pure water in an amount of 10 times the amount of the calcined hydroxyapatite particles on weight basis was added to the calcined hydroxyapatite particles, and the resulting mixture was subjected to ultrasonic cleaning. After cleaning by pure water was repeated 3 times, the obtained mixture was dried at 60° C. to remove moisture contained in the calcined hydroxyapatite particles. After the particles were dried overnight, the calcined hydroxyapatite particles were sequentially sieved by using a sieve having an opening of 100 μm and a sieve having an opening of 38 μm to collect substances remaining on the sieve having an opening of 38 μm to obtain an adsorbent.

Example 2

An adsorbent was produced in a manner similar to Example 1 except that the calcination temperature was changed to 200° C.

Example 3

An adsorbent was produced in a manner similar to Example 1 except that the calcination temperature was changed to 300° C.

Example 4

An adsorbent was produced in a manner similar to Example 1 except that the calcination temperature was changed to 400° C.

Example 5

An adsorbent was produced in a manner similar to Example 1 except that the calcination temperature was changed to 500° C.

Example 6

An adsorbent was produced in a manner similar to Example 1 except that the calcination temperature was changed to 600° C.

Example 7

An adsorbent was produced in a manner similar to Example 1 except that the calcination temperature was changed to 700° C.

Comparative Example 1

An adsorbent was produced in a manner similar to Example 1 except that the calcination step was omitted.

Particles obtained in Comparative Example 1 were unstable, and unable to withstand actual use as an adsorbent as it was.

Comparative Example 2

An adsorbent was produced in a manner similar to Example 1 except that the calcination temperature was changed to 800° C.

Comparative Example 3

An adsorbent was produced in a manner similar to Example 1 except that the calcination temperature was changed to 900° C.

Comparative Example 4

An adsorbent was produced in a manner similar to Example 1 except that the calcination temperature was changed to 1000° C.

Comparative Example 5

Production of Aggregates of Hydroxyapatite Particles

Hydroxyapatite particles (primary particles) having an average major-axis size of 135 nm (made by Sofsera Corporation) were dispersed into water to be in a concentration of 3% by weight to prepare slurry. The resulting slurry is spray-dried by SPRAY DRYER LB-8 (made by Ohkawara Kakohki Co., Ltd.) to granulate hydroxyapatite particles into aggregates (secondary particles). Upon granulation, formation of fine particles by spraying was performed at a rotating speed 14,000 of a rotary atomizer to obtain a desired particle size. Moreover, spray-drying was performed under conditions in which a hot air temperature at a drying chamber inlet was 200° C., the air speed was 6 m³/minute and the amount of slurry supply to SPRAY DRYERLB-8 was 1700 mL/hr.

Calcination Step

Then, 200 g of the hydroxyapatite secondary particles produced as described above was weighed in an alumina crucible and put in a calcination furnace. The temperature in the furnace was raised to 400° C. at a rate of 10° C. per minute. After the temperature was held at 100° C. for 1 hour, the hydroxyapatite secondary particles were left to cool to about room temperature. Then, a 1% (w/v) aqueous solution of ammonium nitrate in an amount of 10 times the amount of the calcined hydroxyapatite particles on weight base was added to the calcined hydroxyapatite particles, and the resulting mixture was subjected to ultrasonic cleaning while the mixture was stirred for 5 minutes. Subsequently, the filtrate was removed by filtration in vacuum, and pure water in an amount of 10 times the amount of the calcined hydroxyapatite particles on weight base was added to the calcined hydroxyapatite particles, and the resulting mixture was subjected to ultrasonic cleaning. After cleaning with pure water was repeated 3 times, the obtained mixture was dried at 60° C. to remove moisture contained in the calcined hydroxyapatite particles. After the particles were dried overnight, the calcined hydroxyapatite particles were sequentially sieved by a sieve having an opening of 100 μm and a sieve having an opening of 38 μm to collect substances remaining on the sieve having an opening of 38 μm.

Comparative Example 6

An adsorbent was produced in a manner similar to Comparative Example 5 except for the calcination temperature was changed to 600° C.

Comparative Examples 7 and 8

In Comparative Examples 7 and 8, CHT Ceramic Hydroxyapatite (40 μm, Type I), and CHT Ceramic Hydroxyapatite (40 μm, Type II), both of which were purchased from Bio-Rad Laboratories, Inc., were used as adsorbents.

Test Example 1: Measurement of Average Pore Size and Specific Surface Area

With regard to each of the adsorbents in Examples 1 to 7 and Comparative Examples 2, and 4 to 8, an average pore size and a specific surface area were measured. Measurement was carried out by using Auto Pore IV 9520 (made by Micromeritics Instrument Corporation) according to mercury porosimetry. As pre-treatment, the adsorbent was isothermally dried at a temperature of 120° C. for 4 hours. Pressure was applied to 0.392 mL of a sample after being dried to a maximum pressure of 4.45 psia, surface tension of mercury was adjusted to 480 dynes/cm and a contact angle between mercury and the sample was adjusted to 140 degrees to calculate the average pore size and the specific surface area.

Here, the average pore size is expressed in terms of an average value of pore diameters to be calculated from the following equation (1) (Washburn equation) in the range of 0.0018 to 0.95 μm at during mercury penetration. Moreover, the specific surface area is expressed in terms of an average value calculated from equation (2).

(pore diameter)=−4×(surface tension of mercury)× cos(contact angle of mercury and sample)/(pressure)    Equation (1)

(specific surface area}=2×(press-in volume of mercury)/(pore radius)/(sample weight)/(degree of swelling)    Equation (2)

The results are shown in Table 1.

TABLE 1

| | Calcination temperature (° C.) | Pore characteristics | |
|---|---|---|---|
| | | Average pore size (nm) | Specific surface area (m²/mL) |
| Example 1 | 100 | 16.5 | 78.1 |
| Example 2 | 200 | 18.0 | 68.6 |
| Example 3 | 300 | 19.3 | 65.9 |
| Example 4 | 400 | 19.9 | 63.8 |
| Example 5 | 500 | 20.6 | 59.9 |
| Example 6 | 600 | 22.5 | 55.1 |
| Example 7 | 700 | 30.0 | 43.7 |
| Comparative Example 2 | 800 | 38.4 | 32.6 |
| Comparative Example 4 | 1000 | 54.8 | 21.2 |
| Comparative Example 5 | 400 | 55.0 | 32.8 |
| Comparative Example 6 | 600 | 64.8 | 27.8 |
| Comparative Example 7 | — | 39.2 | 42.4 |
| Comparative Example 8 | — | 63.2 | 26.7 |

Test Example 2: Measurement of Dynamic Binding Capacity of Lysozyme

Dynamic binding capacity of lysozyme was measured on the adsorbents in Examples 1 to 7 and Comparative Examples 2 to 8. Each adsorbent was packed into a 6.6 mmϕ Omnifit glass column to a height of 3 cm, and the column was connected to a medium pressure liquid chromatography system. Then, 10 CV (column volume) of 500 mmol/L sodium phosphate buffer solution (pH 6.5) was passed through The connected column, and then a 5 mmol/L sodium phosphate buffer solution (pH 6.5) was passed therethrough to equilibrate the column until absorbance at 280 nm and electrical conductivity of a column effluent were stabilized. Next, lysozyme (weight average molecular weight: 14 kDa, made by Wako Pure Chemical Industries, Ltd.) was dissolved into a 5 mmol/L sodium phosphate buffer solution to be in a concentration of 1 mg/mL (pH 6.5) to prepare a lysozyme solution. The lysozyme solution was flowed through the column packed with the adsorbent at a flow rate 0.25 mL/min (retention time: 4 minutes) to calculate 10% dynamic binding capacity by using the following equation by applying the absorbance (at 280 nm) of the column effluent as an indication. Here, "10% dynamic binding capacity" means a lysozyme loading amount per column volume at a time point at which absorbance in a concentration corresponding to a 10% concentration of lysozyme solution loaded to the column (namely, a lysozyme amount adsorbed on the column) in measuring the absorbance of the column effluent.

(Lysozyme loading amount (mL) at a time point at which absorbance in a concentration corresponding to a lysozyme concentration of 0.1 mg/mL was detected−dead volume (mL))/(column volume)=10% dynamic binding capacity (mg/mL), where, the dead volume is a volume obtained by adding a system piping volume and a column void volume (mL), and the system piping volume is a volume obtained by adding volumes of piping for connecting a column and a liquid chromatography system, pipings in the liquid chromatography system, flow paths in valves and a UV meter and so forth.

The measurement results of dynamic binding capacity of lysozyme are shown in Table 2.

TABLE 2

|  | Calcination temperature (° C.) | 10% dynamic binding capacity of lysozyme (mg/mL) |
|---|---|---|
| Example 1 | 100 | 67.4 |
| Example 2 | 200 | 58.7 |
| Example 3 | 300 | 55.5 |
| Example 4 | 400 | 54.8 |
| Example 5 | 500 | 50.4 |
| Example 6 | 600 | 44.0 |
| Example 7 | 700 | 38.4 |
| Comparative Example 2 | 800 | 30.0 |
| Comparative Example 3 | 900 | 10.0 |
| Comparative Example 4 | 1000 | 1.2 |
| Comparative Example 5 | 400 | 14.0 |
| Comparative Example 6 | 600 | 13.0 |
| Comparative Example 7 | — | 31.0 |
| Comparative Example 8 | — | 17.5 |

As shown in Table 2, a larger amount of lysozyme can be adsorbed on the adsorbents of the invention, and the adsorbents can be reasonably described to be useful for purification of a protein having a molecular weight comparable with the molecular weight of lysozyme.

Test Example 3: Measurement of Dynamic Binding Capacity of Fragmented Antibody (Fab Fragments)

Preparation of Fab Fragments

Then, 3 g of γ-globulin (derived from human serum, made by Wako Pure Chemical Industries, Ltd.) was dissolved into a mixture of 25 mmol/L sodium phosphate, 20 mmol/L cysteine and a 2 mmol/L EDTA buffer solution (pH 7.5) to be in a concentration of 10 mg/mL. Papain from papaya latex (made by Sigma-Aldrich Corporation) was added to the resulting mixture to be in an enzyme unit of 100 mU, and enzymolysis was performed at 37° C. After 4 hours, iodoacetamide (made by Wako Pure Chemical Industries, Ltd.) was added to be in a final concentration of 20 mmol/L, and the enzymatic reaction was stopped. The reaction solution was replaced with a mixture of 20 mmol/L sodium phosphate and a 150 mmol/L sodium chloride buffer solution (pH 7.2) by using an ultrafiltration module ACP-1013 (made by Asahi Kasei Co. Ltd.) to prepare a polyclonal antibody enzyme decomposition product to be in a protein concentration of about 10 mg/mL.

Next, protein A-immobilized carrier KanCapA (made by Kaneka Corporation) was packed in an 11 mmϕ glass column to a height of 18 cm, and the column was connected to a medium pressure liquid chromatography system. Then, a mixture of 20 mmol/L sodium phosphate and a 150 mmol/L sodium chloride buffer solution (pH 7.2) was passed through a connected column to equilibrate the column until absorbance at 280 nm and electrical conductivity of a column effluent were stabilized. Subsequently, the polyclonal enzymatic decomposition product prepared as described above was passed through the column at a flow rate of 3.0 mL/min to collect an effluent thereof. The collected effluent was replaced with a 5 mmol/L sodium phosphate buffer solution (pH 6.5) by using an ultrafiltration module ACP-1013 (made by Asahi Kasei Co. Ltd.) to prepare a protein A carrier elution fraction to be in a protein concentration of about 5 mg/mL.

In order to perform further purification, the media in Comparative Example 2 was packed into a 22 mmϕ glass column to a height of 7.5 cm, and the glass column was connected to a medium pressure liquid chromatography system. Then, a 5 mmol/L sodium phosphate buffer solution (pH 6.5) was passed through the connected column to equilibrate the column until absorbance at 280 nm and electrical conductivity of a column effluent were stabilized. Subsequently, the protein A carrier elution fraction prepared as described above was flowed through the column at a flow rate of 5.0 ml/min, and then a non-adsorbed product was washed with a 5 mmol/L sodium phosphate buffer solution (pH 6.5). Further, a mixture of 5 mmol/L sodium phosphate and a 1 mol/L sodium chloride buffer solution (pH 6.5) was flowed through the column to collect an effluent thereof. The collected effluent was dialyzed using a cellulose membrane having a fractional molecular weight of 12,000 to 14,000 in a 5 mmol/L sodium phosphate buffer solution (pH 6.5), and the resulting Fab fragments (weight average molecular weight: 50 kDa) were used in measure the dynamic binding capacity.

Measurement of Dynamic Binding Capacity

The adsorbents in Examples 1 to 7 and Comparative Examples 2 to 8 were packed into a 6.6 mmϕ Omnifit glass column to a height of 3 cm, and the column was connected to a medium pressure liquid chromatography system. Then, 10 CV (column volume) of a 500 mmol/L sodium phosphate buffer solution (pH 6.5) was passed through the column, and then a 5 mmol/L sodium phosphate buffer solution (pH 6.5) was passed therethrough to equilibrate the column until absorbance at 280 nm and electrical conductivity of a column effluent were stabilized. Meanwhile, a sample of the Fab fragments prepared as described above was dissolved into a 5 mmol/L sodium phosphate buffer solution to be in a concentration of 1 mg/mL (pH 6.5) to prepare a solution of Fab fragments. The solution of Fab fragments was passed through the column packed with the absorbents (retention time: 4 minutes) at a flow rate of 0.25 ml/min to calculate 10% dynamic binding capacity was calculated by using the following equation by applying the absorbance (at 280 nm) of the column effluent as an indication. Here, "10% dynamic binding capacity" means a Fab fragments loading amount per column volume at a time point at which absorbance in a concentration corresponding to a 10% concentration of Fab fragments solution loaded to the column (namely, an amount of Fab fragments adsorbed on the column) was detected in measuring the absorbance of the column effluent.

(Fab fragments loading amount (mL) at a time point at which absorbance in a concentration corresponding to a concentration of 0.1 mg/mL of Fab fragments was detected−dead volume (mL))/(column volume)=10% dynamic binding capacity (mg/mL), where, the dead volume is a volume obtained by adding a system piping volume and a column void volume (mL).

The results are shown in Table 3.

TABLE 3

| | Calcination temperature (° C.) | 10% dynamic binding capacity of Fab fragments (mg/mL) |
|---|---|---|
| Example 1 | 100 | 44.4 |
| Example 2 | 200 | 44.6 |
| Example 3 | 300 | 47.8 |
| Example 4 | 400 | 49.0 |
| Example 5 | 500 | 40.0 |
| Example 6 | 600 | 44.5 |
| Example 7 | 700 | 33.4 |
| Comparative Example 2 | 800 | 27.3 |
| Comparative Example 3 | 900 | 13.7 |
| Comparative Example 4 | 1000 | 8.8 |
| Comparative Example 5 | 400 | 20.3 |
| Comparative Example 6 | 600 | 18.0 |
| Comparative Example 7 | — | 31.9 |
| Comparative Example 8 | — | 17.1 |

As shown in Table 3, a larger amount of Fab fragments can be adsorbed on the adsorbents of the invention, and the adsorbents are reasonably described to be useful for purification of a protein having a molecular weight comparable with the molecular weight of Fab fragments.

Test Example 4: Measurement of Dynamic Binding Capacity of α-Chymotrypsinogen A

Dynamic binding capacity of α-chymotrypsinogen A was measured on the adsorbents in Examples 1 to 7 and Comparative Examples 2 to 8. Each adsorbent was packed into a 6.6 mmφ Omnifit glass column to a height of 3 cm, and the column was connected to a medium pressure liquid chromatography system. Then, 10 CV (column volume) of a 500 mmol/L sodium phosphate buffer solution (pH 6.5) was passed through the connected column, and then a 5 mmol/L sodium phosphate buffer solution (pH 6.5) was passed therethrough to equilibrate the column until absorbance at 280 nm and electrical conductivity of a column effluent were stabilized. Next, α-chymotrypsinogen A (weight average molecular weight: 25 kDa, made by Sigma-Aldrich Corporation) was dissolved into a 5 mmol/L sodium phosphate buffer solution to be in a concentration of 1 mg/mL (pH 6.5) to prepare an α-chymotrypsinogen A solution. The α-chymotrypsinogen A solution was flowed through the column packed with the absorbents (retention time: 4 minutes) at a flow rate of 0.25 mL/min to calculate 10% dynamic binding capacity by using the following equation by applying the absorbance (at 280 nm) of the column effluent as an indication. Here, "10% dynamic binding capacity" means an α-chymotrypsinogen A loading amount per column volume at a time point at which absorbance in a concentration corresponding to a 10% concentration of α-chymotrypsinogen A solution loaded to the column (namely, an amount of α-chymotrypsinogen A adsorbed on the column) in measuring the absorbance of the column effluent.

{α-Chymotrypsinogen A loading amount (mL) at a time point at which absorbance in a concentration corresponding to an α-chymotrypsinogen A concentration of 0.1 mg/mL−dead volume (mL)}/(column volume)=10°, dynamic binding capacity (mg/mL), where, the dead volume is a volume obtained by adding a system piping volume and a column void volume (mL), and the system piping volume is a volume obtained by adding volumes of pipings for connecting a column and a liquid chromatography system, pipings in the liquid chromatography system, flow paths of valves and a UV meter and so forth.

The measurement results of dynamic binding capacity of α-chymotrypsinogen A are shown in Table 4.

TABLE 4

| | Calcination temperature (° C.) | 10% dynamic binding capacity of α-chymotrypsinogen A (mg/mL) |
|---|---|---|
| Example 1 | 100 | 92.0 |
| Example 2 | 200 | 83.6 |
| Example 3 | 300 | 105.2 |
| Example 4 | 400 | 94.0 |
| Example 5 | 500 | 96.8 |
| Example 6 | 600 | 73.4 |
| Example 7 | 700 | 71.0 |
| Comparative Example 2 | 800 | 60.6 |
| Comparative Example 3 | 900 | 26.4 |
| Comparative Example 4 | 1000 | 17.6 |
| Comparative Example 5 | 400 | 42.4 |
| Comparative Example 6 | 600 | 36.0 |
| Comparative Example 7 | — | 60.2 |
| Comparative Example 8 | — | 37.2 |

As shown in Table 4, a larger amount of α-chymotrypsinogen A can be adsorbed on the adsorbents of the invention, and the adsorbents can be reasonably described to be useful for purification of a protein having a molecular weight comparable with the molecular weight of α-chymotrypsinogen A.

Several embodiments of the present invention are described, but the embodiments are presented as examples, and not intended to limit the scope of the invention. The new embodiments described herein may be embodied in various other forms, without departing from the scope of the invention, various omissions, substitutions and alternations can be made. The embodiments and their modifications fall within the scope and spirit of the invention, and are included in the invention as described in the appended claims and in the scope of their equivalents.

The invention claimed is:

1. An adsorbent, comprising aggregates of calcium phosphate-based particles and having an average pore size of 15 to 24 nanometers and a specific surface area of 50 to 90 $m^2$/mL when measurement is carried out by mercury porosimetry.

2. The adsorbent according to claim 1, wherein the calcium phosphate-based particles are hydroxyapatite particles.

3. The adsorbent according to claim 1, wherein the calcium phosphate-based particles have an average major-axis size of 20 to 50 nanometers.

4. The adsorbent according to claim 1, being used as a media for chromatography for isolation and purification of a biomolecule.

5. The adsorbent according to claim 4, wherein the biomolecule is a protein.

6. The adsorbent according to claim 5, wherein the protein has a weight average molecular weight less than 60 kDa.

7. The adsorbent according to claim 6, wherein dynamic binding capacity of the protein is 40 mg/mL or more in a retention time of 4 minutes.

8. The adsorbent according to claim 7, wherein the protein is a fragmented antibody, and the dynamic binding capacity is 40 mg/mL or more.

9. The adsorbent according to claim 7, wherein the protein is lysozyme, and the dynamic binding capacity is 40 mg/mL or more.

10. The adsorbent according to claim 7, wherein the protein is α-chymotrypsinogen A, and the dynamic binding capacity is 70 mg/mL or more.

11. A media for chromatography, comprising the adsorbent according to claim 1.

12. A method for purifying a biomolecule, comprising:
packing a column with the adsorbent according to claim 1;
passing a solution containing the biomolecule into the column; and
eluting the biomolecule in the column and collecting the biomolecule.

13. The method according to claim 12, wherein the biomolecule is a protein.

14. The method according to claim 13, wherein the protein is a fragmented antibody.

15. The method according to claim 14, wherein the fragmented antibody is a Fab fragment.

16. A method for producing an adsorbent, comprising:
(a) spray-drying slurry containing calcium phosphate-based particles having an average major-axis size of 20 to 50 nanometers to obtain aggregates of calcium phosphate-based particles, and
(b) calcining the aggregates of calcium phosphate-based particles at a temperature of 100 to 600° C.,
wherein the produced adsorbent comprises aggregates of calcium phosphate-based particles and has an average pore size of 15 to 24 nanometers and a specific surface area of 50 to 90 $m^2$/mL when measurement is carried out by mercury porosimetry.

* * * * *